(12) United States Patent
Morad et al.

(10) Patent No.: US 11,839,534 B2
(45) Date of Patent: Dec. 12, 2023

(54) APPARATUS AND METHOD TO DISPENSE SANITARY HYGIENE PRODUCTS

(71) Applicant: TRANZONIC COMPANIES, Cleveland, OH (US)

(72) Inventors: Fred I. Morad, Toluca Lake, CA (US); Robert A. Acosta, Norwalk, CA (US)

(73) Assignee: TRANZONIC COMPANIES, Cleveland, OH (US)

( * ) Notice: Subject to any disclaimer, the term of this patent is extended or adjusted under 35 U.S.C. 154(b) by 0 days.

(21) Appl. No.: 17/670,636

(22) Filed: Feb. 14, 2022

(65) Prior Publication Data

US 2022/0160555 A1    May 26, 2022

Related U.S. Application Data

(60) Continuation of application No. 17/380,717, filed on Jul. 20, 2021, now Pat. No. 11,246,771, which is a
(Continued)

(51) Int. Cl.
*A61F 15/00* (2006.01)
*A61F 13/551* (2006.01)
(Continued)

(52) U.S. Cl.
CPC ........ *A61F 15/003* (2013.01); *A61F 13/5514* (2013.01); *A61F 13/55175* (2013.01);
(Continued)

(58) Field of Classification Search
CPC ..... A61B 5/1117; A61B 5/0022; A61B 5/024; A61B 5/7264; A61B 2562/0219; G16H 40/67; G16H 40/63; G16H 20/13; G06N 20/00; G06F 15/76; G07F 15/10; G07F 11/045; G07F 11/005; G07F 11/10;
(Continued)

(56) References Cited

U.S. PATENT DOCUMENTS

| 5,555,965 A * | 9/1996 | Mishina ................ A61F 15/003 221/6 |
| 5,605,249 A * | 2/1997 | Gonyea ................... G07F 11/54 221/121 |

(Continued)

FOREIGN PATENT DOCUMENTS

| CA | 2342260 C * | 3/2009 | ............. A47K 10/36 |
| CA | 2983190 A1 * | 4/2018 | ........... A61F 15/001 |

(Continued)

*Primary Examiner* — Rakesh Kumar
(74) *Attorney, Agent, or Firm* — Taft Stettinius & Hollister LLP; Ryan O. White; Daniel J. Krieger

(57) ABSTRACT

A dispenser of hygiene products, including feminine pads and tampons activated by a motion sensor. A motion of a person's hand or other object within a given distance from the motion sensor will close an electronic circuit causing a motor to rotate. The motor is attached to a shaft which rotates. The shaft retains a product dispenser. The product dispenser transports one of the hygiene products to a retrieval tray. A time delay reduces the likelihood of or prevents someone from continuously activating the motion sensor to dispense all of the products in the machine.

19 Claims, 10 Drawing Sheets

Related U.S. Application Data division of application No. 16/056,922, filed on Aug. 7, 2018, now Pat. No. 11,185,453.

(60) Provisional application No. 62/613,345, filed on Jan. 3, 2018.

(51) Int. Cl.
*G07F 11/00* (2006.01)
*G07F 11/04* (2006.01)
*G07F 17/00* (2006.01)
*G07F 11/10* (2006.01)
*G07F 17/18* (2006.01)

(52) U.S. Cl.
CPC .......... *G07F 11/005* (2013.01); *G07F 11/045* (2013.01); *G07F 11/10* (2013.01); *G07F 17/0092* (2013.01); *G07F 17/18* (2013.01); *A61F 2013/55195* (2013.01)

(58) Field of Classification Search
CPC .... G07F 17/0092; G07F 17/18; A61F 15/003; A61F 13/5514; A61F 13/55175; A61F 2013/55195
USPC ........ 700/237, 231; 221/15, 129, 6; 197/217
See application file for complete search history.

(56) References Cited

U.S. PATENT DOCUMENTS

| | | | | |
|---|---|---|---|---|
| 6,556,889 | B2 * | 4/2003 | Rudick | G07F 11/42 700/242 |
| 6,695,246 | B1 * | 2/2004 | Elliott | A47K 10/36 242/563.2 |
| 7,296,765 | B2 * | 11/2007 | Rodrian | G07F 5/22 242/563.2 |
| 9,057,997 | B2 * | 6/2015 | Ogata | H04N 1/00323 |
| 2012/0167739 | A1 * | 7/2012 | Lewis | B26D 5/00 83/663 |
| 2012/0234858 | A1 * | 9/2012 | Ophardt | A47K 5/1217 222/23 |
| 2013/0086741 | A1 * | 4/2013 | Bayley | F26B 21/12 34/443 |
| 2015/0238053 | A1 * | 8/2015 | Yang | B65D 25/00 222/173 |
| 2015/0238056 | A1 * | 8/2015 | Fellhoelter | A47K 10/3687 242/560 |
| 2016/0000274 | A1 * | 1/2016 | Byrd | A47K 10/36 242/563.2 |
| 2021/0043023 | A1 * | 2/2021 | Coder | G07F 11/005 |

FOREIGN PATENT DOCUMENTS

| | | | | |
|---|---|---|---|---|
| WO | WO-2006060047 | A1 * | 6/2006 | A47K 10/36 |
| WO | WO-2011059423 | A1 * | 5/2011 | A47K 10/36 |
| WO | WO-2012007773 | A2 * | 1/2012 | A23G 9/045 |

* cited by examiner

APPARATUS AND METHOD TO DISPENSE SANITARY HYGIENE PRODUCTS

CROSS-REFERENCE TO RELATED APPLICATION

This application is a continuation patent application of U.S. patent application Ser. No. 17/380,717, entitled Apparatus and Method to Dispense Feminine Hygiene Products Using a Motion Sensor, which is a divisional patent application of U.S. patent application Ser. No. 16/056,922, entitled Apparatus and Method to Dispense Feminine Hygiene Products Using a Motion Sensor, filed Aug. 7, 2018, which claims priority to Provisional Patent Application Ser. No. 62/613,345, filed Jan. 3, 2018, and Provisional Patent Application Ser. No. 62/570,596 filed Oct. 10, 2017, the disclosures of which are each incorporated by reference herein in their entirety.

FIELD OF THE DISCLOSURE

The present invention relates to a machine that dispenses a product, and more particularly relates to a vending machine that dispenses one or more hygiene products.

BACKGROUND

U.S. Pat. No. 9,721,419 entitled "Vending Machine for Retaining and Dispensing Feminine Hygiene Products Through a Novel Coin Operating Apparatus", describes a coin-operating vending machine that allows a user to purchase a feminine hygiene product with a coin. In a free condition, product is dispensed with a time delay to prevent users from rapidly removing all of the products.

U.S. Pat. No. 9,501,888 entitled "Vending Machine for Retaining and Dispensing Feminine Hygiene Products Through a Novel Coin Operating Apparatus", describes a coin operated vending machine that allows a user to purchase a feminine hygiene product with a coin and by pressing a product release button.

SUMMARY

The present invention is a vending machine which contains two columns of feminine hygiene products adjacent one another, with a first feminine hygiene product, such as sanitary pads in one column, and a second feminine hygiene product, such as tampons, in a second column. The products are aligned in rails, one product above another product within the column of products. There is a weight on top of each column of products to provide a downward force to enable the next successive product to be placed in condition for dispensing, after the lowermost product has been dispensed. The rails have a rear surface and a pair of side rails which envelope the specific packaging in which each respective feminine hygiene product is retained.

There is an aligned horizontal dispensing platform on which the lowest feminine hygiene product is retained with opposite blocking members which assist in dispensing the retained lowermost feminine hygiene product. The opposite blocking members assist in receiving the next lowermost feminine hygiene product on an oppositely disposed receiving platform. Each column further includes a top weight bearing platform with a magnetic sensor thereon which forces the second lowermost feminine hygiene product into a receiving platform after the lowermost feminine hygiene product has been dispensed into a product accessory receiving tray from which the packaged feminine hygiene product is removed by a person.

The operation of the vending machine is controlled by a computer chip in a motherboard. A left motion sensor, also referred to as a first feminine hygiene product motion sensor, is affixed to the rear of a front door and contains three wire leads which are connected to respective female connectors on the motherboard. In one embodiment, the first feminine hygiene product is a feminine napkin or feminine pad. A right motion sensor, also referred to as a second feminine hygiene product motion sensor, is also affixed to the rear of the front door and is connected by three wire leads to female connectors on the motherboard. In one embodiment the second feminine hygiene product is a tampon. A power pack, which in one embodiment is a battery pack, and by way of example, can include four "AA" batteries hardwired by two wiring leads from the battery pack to female connectors on the motherboard. Other sources or power are contemplated. A door switch, which is at a lower portion of the door, in one embodiment, is also hardwired to female connectors on the motherboard by a pair of wire leads. A first (feminine napkin) drive motor is hardwired to the motherboard by two wire leads from the left motor or feminine napkin motor to female connectors on the motherboard. A left microswitch with a spring steel extension is also hardwired by two hardwire leads to female connectors on the motherboard. A left reed switch or feminine napkin reed switch is also hardwired to female connectors to the motherboard.

The first feminine hygiene product (the feminine napkin) is retained in a rail in a vertically aligned column of products with a weight on the topmost product with a magnet on top, side, or end of the weight. When the supply of feminine napkins is exhausted and there are no more feminine napkins in the column, the magnet at the top of the feminine napkin column actuates or touches the left reed switch or feminine napkin reed switch to cause a warning light to blink on and off. The warning light can have one or two variations. As shown, the left warning light or feminine napkin warning light is hardwired by two wire leads to female connectors on the motherboard. Therefore, when the rail retaining the column of feminine napkins is out of feminine napkins, the magnet on top of the weight actuates, or in another embodiment, comes in contact with the reed switch at the bottom of the feminine napkin column, the light will blink on and off, and is visible through an opening in the front door. The opening can be at a location where a symbol for the first feminine hygiene product (the feminine napkin) is located on the front door. In an alternative variation, the light, in one or more embodiments, is incorporated into the motion sensor board of the feminine napkin product. The light shines through an opening in the front door and blinks on and off to show that the machine is out of this product. In other embodiments, the light shines through the material of the door, which is sufficiently transparent for the light to be seen by an observer.

Also when a motion is made in front of the motion sensor, this causes the feminine napkin motor to rotate which in turn is connected to a shaft which is in turn connected to a dispensing member which will rotate 180 degrees. After a 180 degree rotation, the spring steel extension from the microswitch, touches the motor, and causes it to stop rotation. Other degrees of rotation are contemplated.

With respect to the second feminine hygiene product (e.g. tampons), the second motor, or right motor, is hardwired by two wire leads to the female connectors on the motherboard. A right microswitch or tampon microswitch is hardwired by two wire leads connected to the female connectors on the motherboard. A second rail, which retains a column of tampons, also has a weight on the column of tampons and a magnet on the top, the side, or an end of the weight. When a motion causes activation through the tampon sensor, the tampon motor rotates by 180 degrees causing a lowermost tampon to be dispensed into a receiving tray. Other degrees of rotation are contemplated.

A second feminine hygiene product (e.g. tampon) reed switch has a metal spring connector which comes in contact with the motor and causes it to stop after a 180 degree rotation. At the bottom of the tampon column there is right or tampon reed switch and when the tampon column is completely out of product, the magnet at the top of the tampon column actuates or, in another embodiment, comes in contact with and touches the tampon reed switch causing a light to be visible through an opening in the front door to blink on and off. The light can either be a separate light which is a tampon light which can shine through an opening in the front door or alternatively, can be built into the motion sensor for the tampon and shine through an opening in the front door aligned with the motion sensor for the tampon. In other embodiments, the light shines through the material of the door, which is sufficiently transparent for the light to be seen by an observer.

The dispensing of products is controlled by a computer chip in the motherboard. In addition, once the front door is opened, for whatever reason such as for restocking product, after the front door is closed, there is a time delay before the machine is operable. The time delay can be anywhere from two seconds to thirty seconds, with a preferred time delay being around fifteen seconds. After this time has elapsed, the machine is operable and product can be dispensed. Also, built into the computer is a time delay so that someone cannot empty the machine by continuous motion for dispensing either feminine napkins or tampons. Once a product, such as a feminine napkin, is dispensed, the computer program causes a time delay of anywhere from two seconds to thirty seconds, with a preferred time delay being around six seconds, before either another feminine napkin or a tampon can be dispensed. Therefore, the time delay causes an inability to immediately activate the machine to dispense a second product, and the time delay reduces the likelihood of or prevents someone from continuously activating the motion sensor to dispense all of the products in the machine. The time delay works both ways for both products. If a tampon is dispensed, then the time delay prevents a second tampon or a first feminine napkin from being dispensed until the computer set time such as two seconds to thirty seconds has elapsed.

A motion in front of a sensor activates the sensor to close an electronic circuit. When the electronic circuit is closed, a motor is activated. The motor is connected to a shaft which retains a feminine hygiene product dispensing member (such as a double tooth or double pin dispenser). The motor causes the shaft to rotate. The shaft retains the feminine hygiene product receiving/retaining and dispensing member, which by way of example, is a double receiving tray. The double receiving tray includes a first horizontal receiving tray above the shaft and a first and second product dispensing member extending from a respective first and second end of the first horizontal receiving tray. The double receiving tray further includes a second horizontal receiving tray below the shaft (relative to the first horizontal receiving tray) and a third and fourth product dispensing member extending from a respective first and second end of the second horizontal receiving tray. In this application, receiving tray is also called a plate or also called a platform.

The lowermost feminine hygiene product in a column of feminine hygiene products rests on the first horizontal receiving tray. Upon activation, the shaft rotates by one-hundred eighty (180) degrees and the first and second product dispensing member combined with gravity cause the lowermost feminine hygiene product to fall into a product retrieving tray. The one-hundred eight (180) degree rotation brings the second horizontal receiving tray into alignment with the column of feminine hygiene products and the weight on top of the column causes the second lowermost feminine hygiene product to fall onto the second horizontal retaining tray between the third and fourth product dispensing members. The micro-switch is an input signal to the motherboard to stop the motor and stop rotation of the shaft after the shaft has rotated one-hundred eighty degrees. Upon a subsequent activation, the cycle is repeated with the second lowermost feminine hygiene product dispensed into the receiving tray and the third lowermost feminine hygiene product now on the first horizontal receiving tray.

Once in the receiving tray, the feminine hygiene product is retrieved by a person. In one or more embodiments, the microswitch monitors the rotation and through a program in the circuit board, causes the motor to turn off which stops the dispensing apparatus after it has completed one cycle, and returns to its initial starting position. When the product dispensing member is returned to its initial starting position, after the first one-hundred eight (180) degree rotation, the apparatus is off until a motion in front of the sensor begins the cycle again. The weight on top of the column causes the second lowermost product in the column to become the lowermost feminine hygiene product which falls onto the second horizontal receiving tray.

The activity for dispensing the feminine hygiene products through a motion action sensor includes, but is not limited to, one or more of the following: (i) a circuit board which contains a motion sensor and has three contact wires; (ii) a first contact hard wired coupled to a source of power such as a pack of batteries; (iii) a second contact hard wired to a microswitch to receive instructions from a program, which is part of the circuit board; and (iv) a third contact hard wired to a motor. Upon activation of the motion sensor, a program in the circuit board causes the motor to turn on causing the motor to operate and causing a shaft to rotate thereby causing the rotation of the affixed dispensing dual tooth (pin) mechanism/apparatus to push the lowermost feminine hygiene product out of the column in which it is located and into a dispensing/receiving tray.

In one embodiment, there is one electronic assembly for each product. There is one circuit board and one set of connectors with connecting wires for the sanitary pads. There is a second separate circuit board and second set of connectors with connecting wires for the tampons.

It is also within the spirit and scope of the present invention to have one circuit board (also called an motherboard), as disclosed herein, which is hardwired to two separate sensors, one for activating and dispensing a sanitary pad, interchangeably referred to herein as a sanitary napkin, and a second for activating and dispensing a tampon. In one embodiment, the retaining elements described in the above paragraph are incorporated in one circuit board (also called the motherboard) with the circuit board configured to send an appropriate product related signal when an associated senor is triggered.

The present invention is preferably housed in a plastic or other comparable container with a cover made of different material and preferably opaque and which facilitates the transmittal of motion to be received by a motion sensor. It is required that the cover to which the sensor is hidden must be made of material to enable the motion sensor to detect the motion. In one embodiment, the cover cannot be made of material which interferes with the sensor's ability to receive and detect a motion to active the motion sensor. The cover cannot be made of material that interferes with the motion activity detectable by the motion sensor. Therefore, a key innovation of the present invention is to have a vending machine with a cover which conceals the circuit boards and sensors on the back of the cover for both the dispensing of sanitary pads and tampons which facilitates the transmission of signals through a printed circuit board to carry out the signals as described above to cause the activation by hand signal. In another embodiment, the cover hiding the sensor includes an aperture over the sensor, such that there is no material to interfere with sensing motion.

In other embodiments, product such as sanitary pads, sanitary towels, panty liners, and bladder control pads are dispensed by the product dispenser.

It is therefore an object of the present invention to have a dispenser to dispense feminine hygiene products including, but not limited to, sanitary napkins and tampons by a simple hand motion without requiring any physical action on the part of the person such as placing coins in the machine or rotating a handle or performing any other comparable physical activity. While such activities may be simple for younger and healthier people, as the population ages, it is more difficult for older people to do the simplest tasks such as rotating a heavy handle or placing the right amount of coins inside a machine. Therefore, by not having to do anything other than wave their hand in front of the appropriate sensor, the difficulty in obtaining a sanitary pad or tampon is substantially reduced.

In an additional embodiment, there is provided an apparatus for dispensing a first feminine hygiene product and a second feminine hygiene product. The apparatus includes: a) a container including a front cover and defining an interior chamber; b) a first rail disposed in the interior chamber having walls to retain a first plurality of the first feminine hygiene product and a second rail having walls to retain a second plurality of the second feminine hygiene product, the first rail disposed adjacently to the second rail; c) a first weight configured to move in and be retained by the first rail and a second weight-configured to move in and be retained by the second rail; d) a first dispenser located at an end of the first rail and a second dispenser located at an end of the second rail, the first dispenser operatively connected to a first motor and the second dispenser operatively connected to a second motor; and e) a first motion sensor, disposed at the front cover, electrically connected to the first motor, and a second motion sensor disposed at the front cover, electrically connected to the second motor, wherein the first motion sensor is configured to actuate the first motor to dispense the first feminine hygiene product in response to a first physical motion, and the second motion sensor is configured to actuate the second motor to dispense the second feminine hygiene product in response to a second physical motion.

In a further embodiment, there is provided a method for dispensing feminine hygiene products from a product dispenser including a door. The method includes: providing one or more motion sensors each being configured to detect a motion provided by a moving object; identifying a delay time; identifying a first time in response to a first motion sensed by one of the motion sensors; dispensing a first product in response to the first motion; identifying a second time in response to a second motion sensed by one of the motion sensors; determining an elapsed time between the first time and the second time; and not dispensing a second product in response to the second motion if the elapsed time is less than the delay time.

In another embodiment, there is provided a method for dispensing feminine hygiene products from a product dispenser including a door, the method including: providing one or more motion sensors each being configured to detect a motion provided by a moving object; identifying a delay time; identifying a first time in response to a first motion sensed by one of the motion sensors; dispensing a first product in response to the first motion; identifying a second time in response to a second motion sensed by one of the motion sensors; determining an elapsed time between the first time and the second time; and not dispensing a second product in response to the second motion if the elapsed time is less than the delay time.

Further novel features and other objects of the present invention will become apparent from the following detailed description and discussion.

BRIEF DESCRIPTION OF THE DRAWINGS

Referring particularly to the drawings for the purpose of illustration only and not limitation, there is illustrated.

DETAILED DESCRIPTION

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention.

Figure 1:
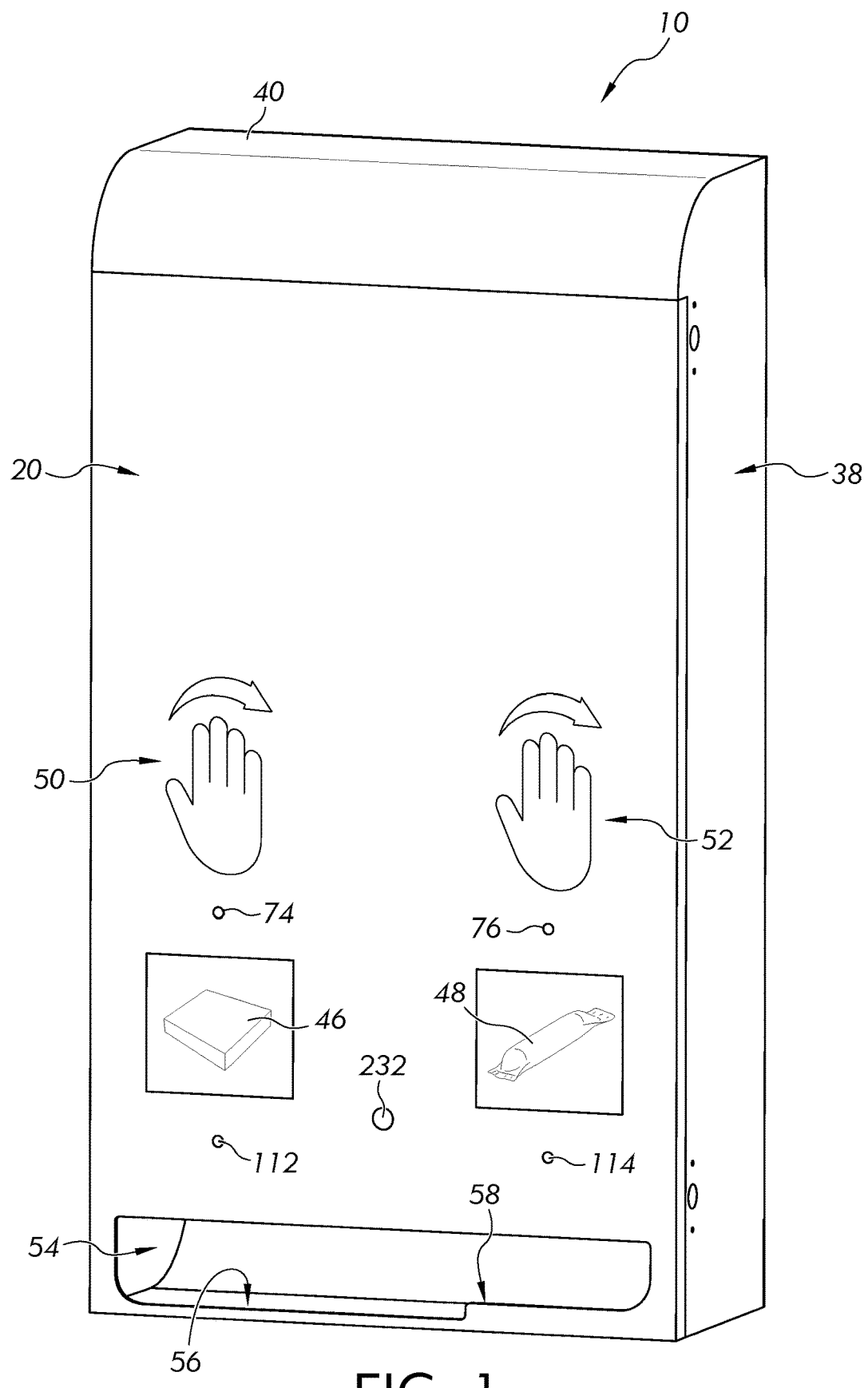
FIG. 1 is a perspective view of a product dispenser including a front cover having a door in a closed condition.
Figure 2:
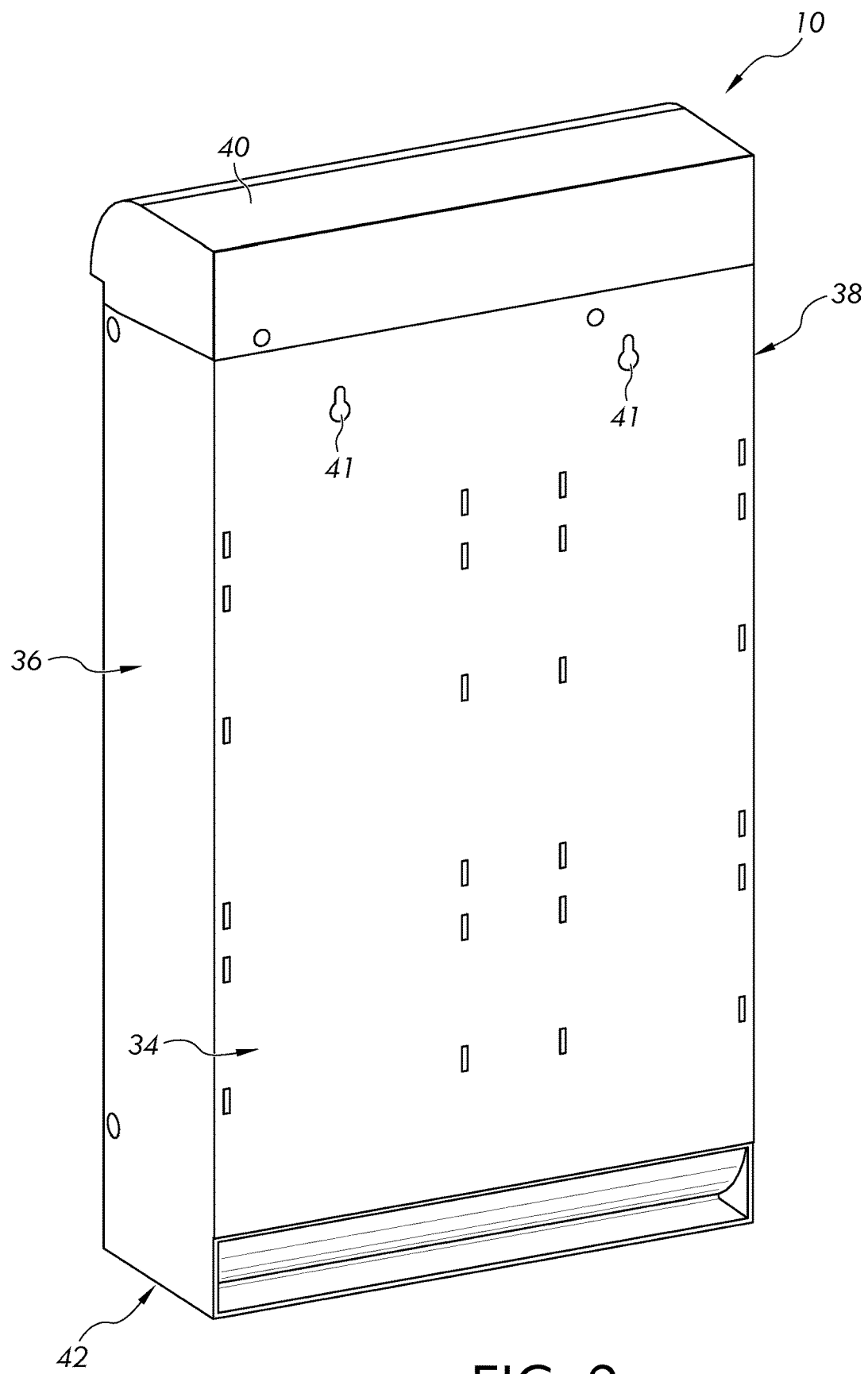
FIG. 2 is a perspective view of a back of the dispenser of FIG. 1.
Figure 3:
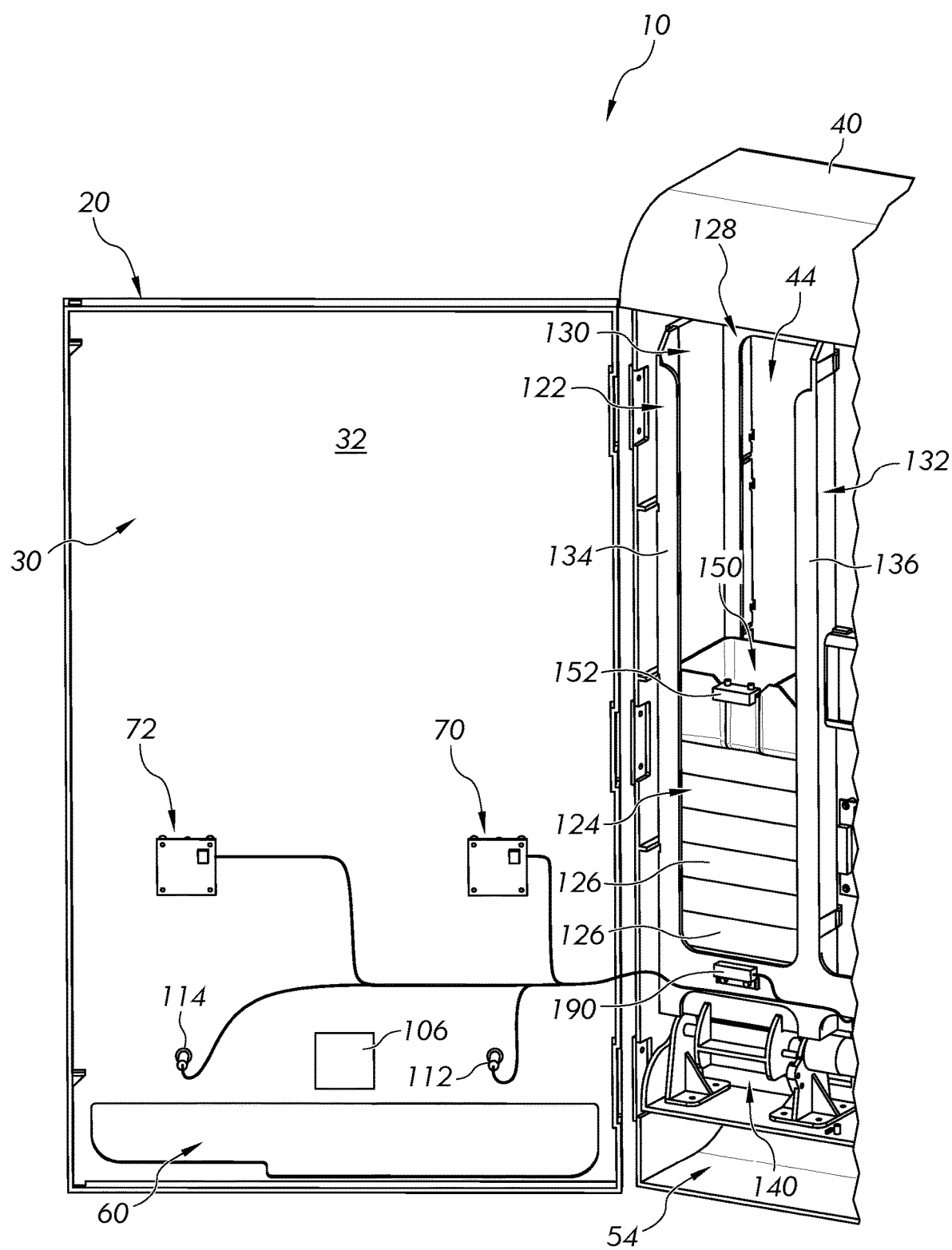
FIG. 3 is an internal perspective view of both sensor circuit boards affixed to a rear surface of a back wall of the cover.

Referring to FIGS. 1, 2, and 3, there is illustrated the a feminine hygiene product dispensing apparatus 10. The apparatus 10 includes a vending type machine with a front door 20, the front door 20 having a back or interior wall 30 with a rear surface 32, as seen in FIG. 3. As shown in FIG. 2, the apparatus 10 further includes a back wall 34 and two sidewalls 36 and 38, a top wall 40 and a bottom wall 42. In one embodiment the back wall 34 includes apertures 41 configured to accept a mounting structure to enable mounting of the dispenser 10 on a wall. The backwall, sidewalls, top wall and bottom wall surround an interior chamber 44 which includes two rails; a first rail having a back wall, a pair of sidewalls and a pair of front walls to retain a vertically aligned column/stack of a first product, i.e. sanitary pads (alternatively called "sanitary napkins and a second rail adjacent the first rail, the second rail having a back wall, a pair of sidewalls and a pair of front walls to retain a vertically aligned column/stack of a second product, i.e. tampons, as described herein.

The front door 20 includes a first product symbol 46 and a second product symbol 48. In one embodiment, the first product symbol 46 is a sanitary napkin symbol and the second product symbol 48 is a tampon symbol. Located on the door 20 and above the symbol 46 is a first motion symbol 50 and above the symbol 48 is a second motion symbol 52. In the illustrated embodiment, each of the motion symbols 50 and 52 are configured as a hand symbol with an arrow to indicate a hand wave which dispenses one of dispense a the first product identified with symbol 46 and a second product identified with symbol 48. Other motion symbols are contemplated. With a first physical motion directed to the first motion symbol 50, the dispenser 10 dispenses the first product, which is retrieved from a tray 54 at a location 56 defined by a bottom surface of the tray 54. With a second physical motion directed to the second motion symbol 52, the dispenser dispenses the second product from the tray at a location 58. The door 20 includes an aperture 60 which in the illustrated embodiment includes cutout features configured to represent a product configuration. For instance, the location 58 is larger than the location 56 to indicated products of different sizes or configurations. In other embodiments, the aperture 60 does not include product configuration feature.

Each of the motion symbols 50 and 52 generally indicate a location of a motion sensor of motion detector 70 and 72, each of which are coupled to the back 32 of the door 20. In one embodiment, the motion sensors are configured to sense the physical movement located near or at the motion symbols 50 and 52 on the outside of the door 20. A first product light 74 illuminates when the sensor 70 detects the physical motion and a second light 76 illuminates when the sensor 72 detects a physical motion. In different embodiments, different types of motion sensors are contemplated including infrared, ultrasonic, and capacitive.

Figure 4:
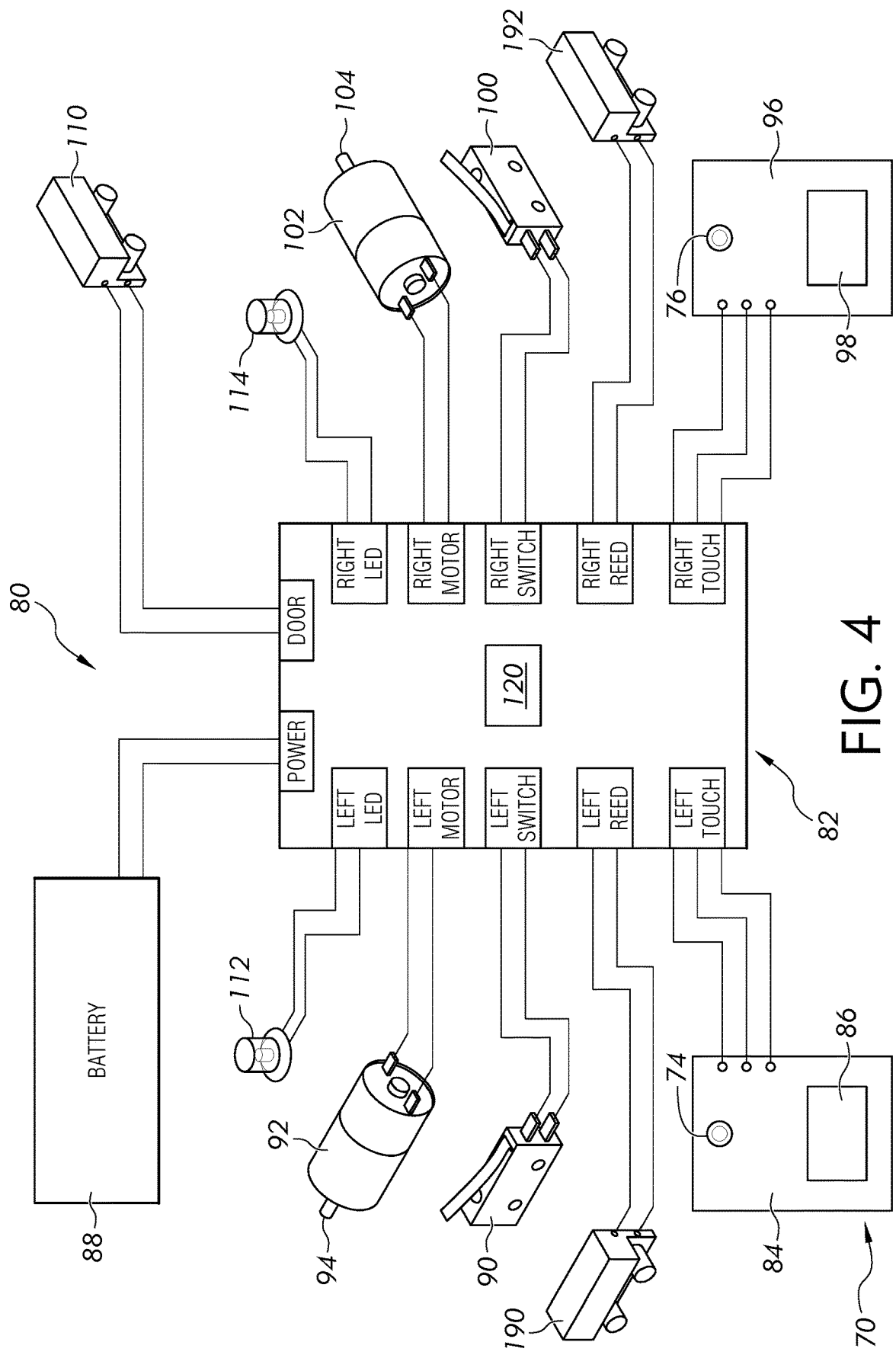
FIG. 4 is a wiring diagram of a motherboard and components which are hardwired by wire leads to female connectors on the motherboard.
Figure 5:
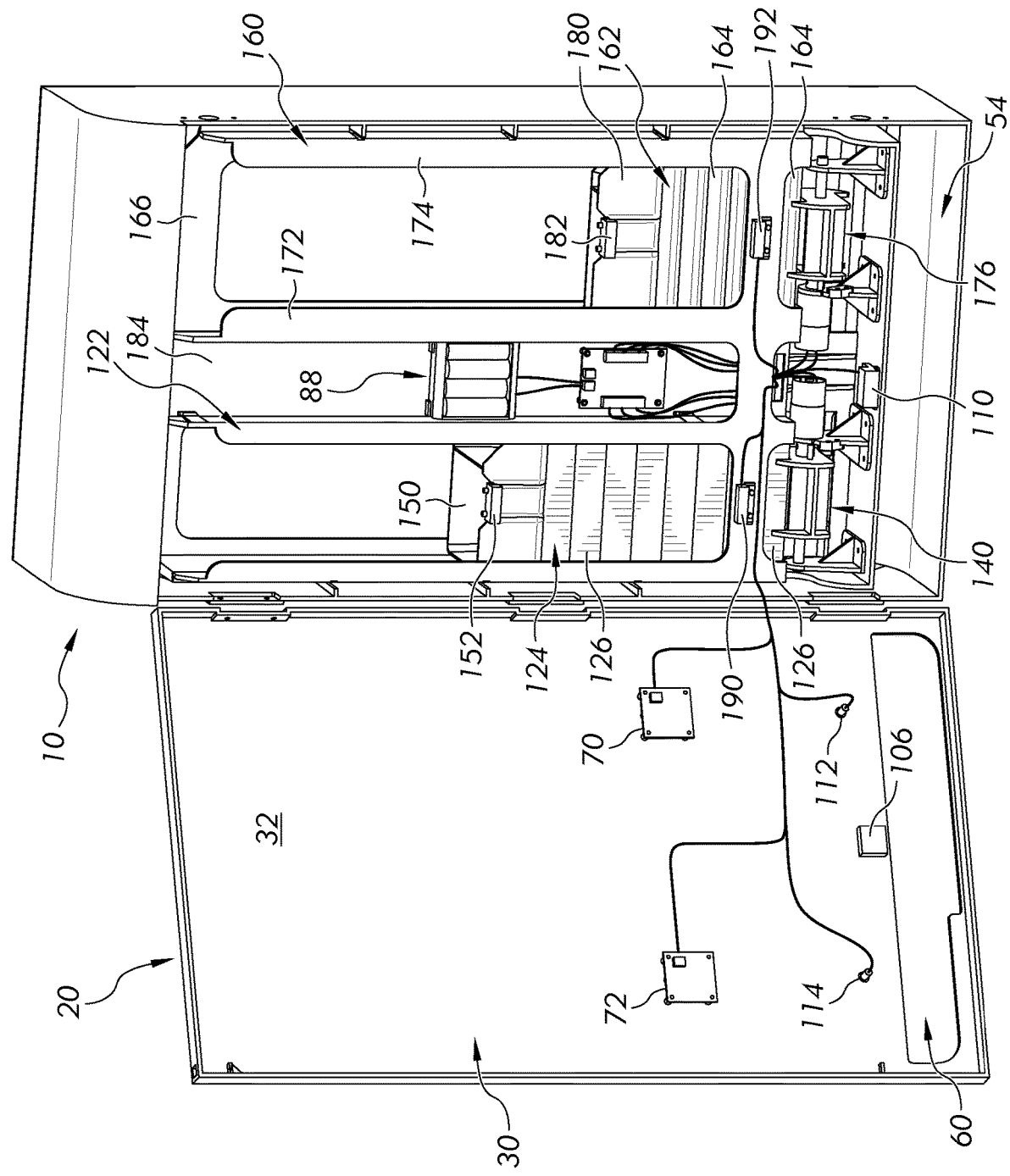
FIG. 5 is an internal perspective view of one embodiment of a dispenser illustrating two separate rails, one rail housing a vertical column of sanitary pads and a second rail housing a vertical column of tampons, a battery power pack, a control circuit board (motherboard) and motors driving a shaft to dispense products.
Figure 6:
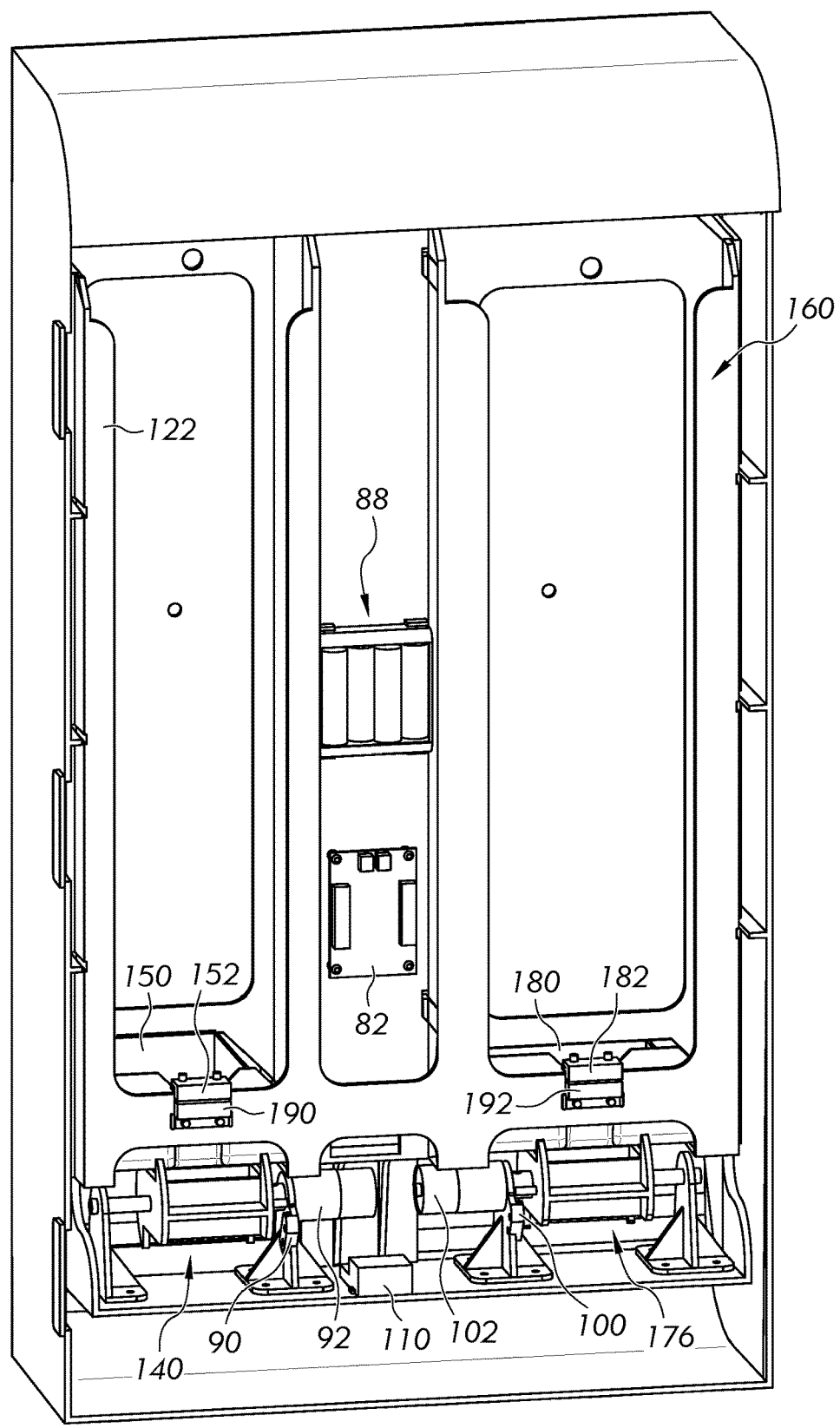
FIG. 6 is an internal front perspective view of a dispenser illustrating two separate rails, a first rail housing and a second rail housing, also illustrating respective product retrieval assemblies under a respective column, illustrating the battery pack, the controller circuit board (motherboard), a respective motor.
Figure 7:
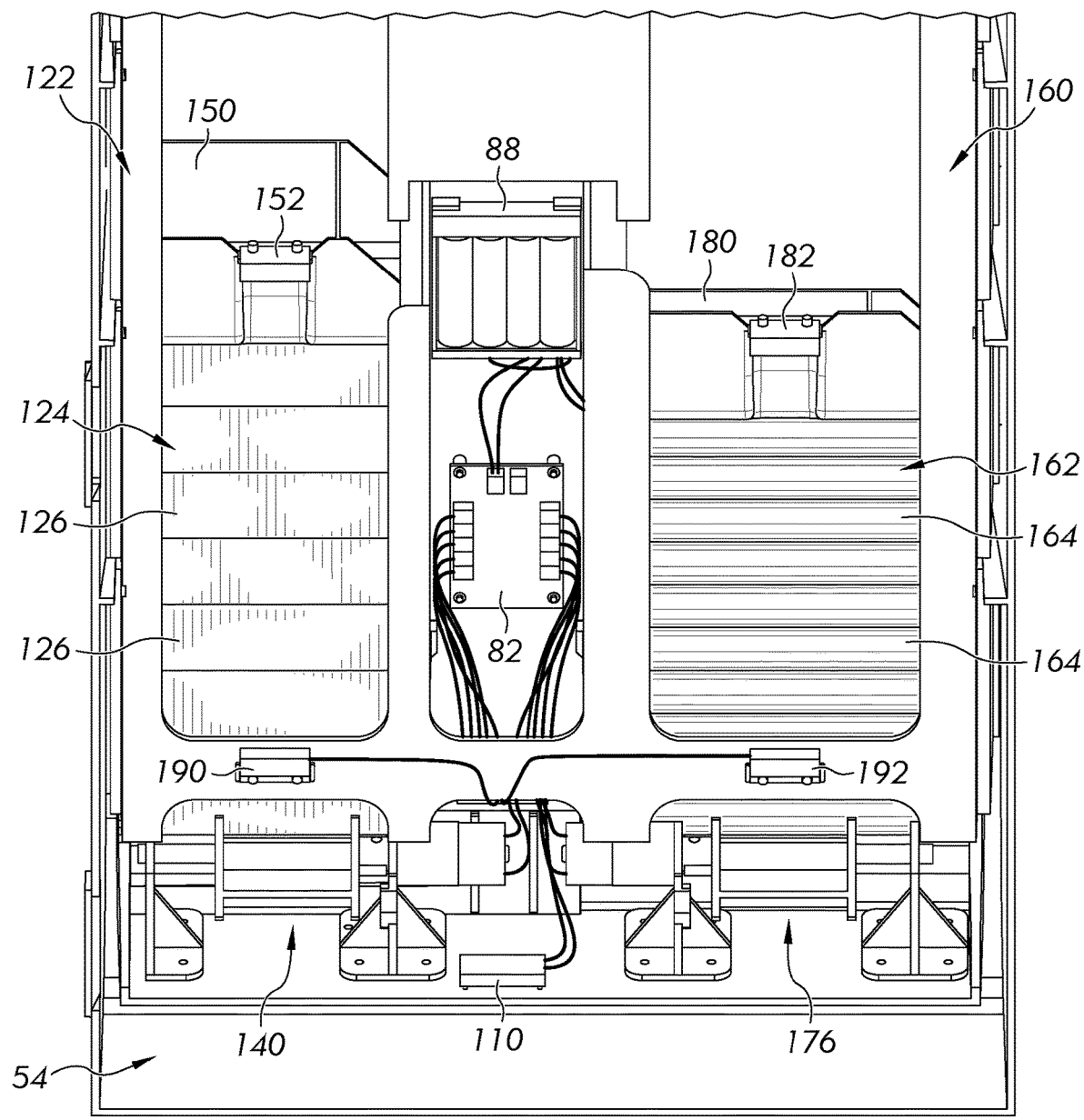
FIG. 7 is a close-up view of the components described in FIG. 6, also illustrating a lowermost sanitary napkin on a first dispenser and a lowermost tampon on a second dispenser.

FIG. 4 illustrates a control system 80 configured to dispense the first product and the second product. FIG. 4 illustrates a wiring diagram of the control system 80 including a motherboard 82 connected to the components of the present invention. FIGS. 5 and 6 further illustrate an open perspective view of the present invention apparatus 10 which includes the components previously described and to a left side, the rotatable front door 20 with a back wall 30 having a rear surface 32. The two sensors 70 and 72 respectively include a respective sensing apparatus which is connected to the motherboard 82 which controls the operation of the apparatus and which motherboard in turn is electrically connected to an operating mechanism for dispensing the products. The motherboard 82 has a multiplicity of female plugs or connectors. Three wire leads from each sensor 70 and 72 are respectively connected to the three respective connectors on the motherboard. Thereafter, two wire leads are respectively connected to other components as will be described.

The first sensor 70 includes a first sensor circuit board 84 which contains therein a first sensor 86 which is hardwired by three wire leads to three respective female connectors on the motherboard 82, also called a contact distribution board or circuit board. A pair of wire leads are hardwired from two respective female connectors on the motherboard 82 to a source of power 88, which by way of example, is a battery pack with four (4) double "AA" batteries. The motherboard 82 is also hardwired by a pair of wire leads from female connectors on the motherboard 82 to a first micro limit switch 90. The motherboard 82 is also hardwired by a pair of wire leads from female connectors on the motherboard 82 to a first drive motor 92. The first driver motor 92 is connected to a first shaft 94. In one embodiment, the switch 90 includes an extending arm, the position of which opens and closes the switch.

The second sensor 72 includes a second sensor circuit board 96 which contains therein a second sensor 98 which is hardwired by three wire leads to three respective female connectors on the motherboard 82. The motherboard 82 is also hardwired by a pair of wire leads from female connectors on the motherboard 82 to a second micro limit switch 100. The motherboard 82 is also hardwired by a pair of wire leads from female connectors on the motherboard 82 to second drive motor 102. The second driver motor 102 is connected to a second shaft 104. In one embodiment, the switch 100 includes an extending arm, the position of which opens and closes the switch.

The power pack 88, in the embodiment shown, contains four "AA" batteries. In other embodiments, the power pack 88 includes any other type or quantity of batteries which would be within the spirit and scope of the present invention. In still other embodiment, the power pack 88 is an internal or external power supply coupled to a source of power, such as 120 VAC or 240 VAC.

Referring to FIGS. 3, 4, and 5, when the door 20 is in the open position, a magnet 106 located near the bottom portion of the rear surface 32 of door 20 is positioned away from a door switch or first reed switch 110 located at the bottom of the rail and motor section. Door switch 110 is hardwired to the motherboard 82 by pair of wire leads connected to female connectors on the motherboard. When door 20 is in the open position light 74 and light 76 blink to indicate that the door is open. The reed switch 110 signals to motherboard 82 whether door 20 is in the open position or in the closed position. A signaling light 112 blinks on and off when the dispenser out of feminine napkins. A second motion sensor light 114 blinks on and off when the dispenser is out of tampons. The lights 112 and 114 are located at apertures on the door 20 and shine through the apertures.

Alternatively, there is another variation of the light 112 and 114 each of which are hardwired by a pair of respective wire leads to female connectors on the motherboard 82. In this variation, the light 112 shines through the symbol of the tampon and the light 114 will shine through the symbol of the feminine napkin on the front door. The door is sufficiently transparent at these locations to transmit light. Therefore, these are two variations where in each case when the apparatus is out of product, the lights will be blinking.

If at least one batteries dies or has reduced power, the motherboard 82 sends a signal to both lights 112 and 114 to illuminate each light steadily and non-blinking.

The motherboard 82 has a computer chip 120 which receives, processes, and transmits all the signals that control all of the operations as discussed. Programmed into the chip are two time delays. First, when the front door 20 is opened for restocking or other purposes, the lights 74 and 76 will show blinking and will not stop blinking until the door is closed. Further, the dispenser 10 is non-operable and therefore, cannot dispense any products. Further, when the door 20 is closed, there is a first time delay anywhere from about 2 seconds to 30 seconds, preferably 15 seconds, wherein the dispenser cannot be operated until that time has elapsed. In addition, programmed into the computer chip 120 is another, or second, time delay wherein if one of the products, either the feminine napkin or the tampons, are dispensed, there is an automatic time delay of anywhere from about 2 seconds to 30 seconds before any other product can be dispensed. In one embodiment, the second time delay is about 15 seconds.

By way of example, if a sanitary napkin is dispensed, then the waiting time, such as 5 seconds must elapse, before either another sanitary napkin or another tampon can be dispensed. Also, if a tampon is dispensed, then again there is the same delay time wherein neither another tampon nor another sanitary napkin can be dispensed. This avoids the machine being emptied by someone continuously waving their hand in front of the machine to extract more products than needed or to extract all of the products within a reasonably short period of time. The delay, under some circumstances, can substantially prevent all of the tampons or sanitary napkins from being dispensed due to each delay.

Through the present invention, an individual, who is handicapped or has difficulty in rotating a knob, or having to place coins in slots, can easily obtain the product by a simple motion of waving a hand in front of the desired sensor. In one embodiment, the sensitivity of the sensor can be set so that the person has to have the motion located within about 1 and ½ inch in front of the sensor. By setting a sensor sensitivity distance, dispensing of products is prevented if someone simply walks by the machine. If the sensitivity is set too sensitive, product could be inadvertently dispensed. The sensitivity is adjustable by the manufacturer during manufacturing or by an installer during installation of the dispenser.

Additionally, there is built into a program, such as a software program or a firmware program, in one of the circuit boards to establish a timing sequence that after a product such as a feminine pad is dispensed, the next successive feminine pad cannot be dispensed for a period of such as 15, 20 or 30 seconds. Similarly, a tampon is dispensed, the next successive tampon cannot be dispensed for a period of time such as 15, 20 or 30 seconds. This will avoid someone from emptying the machine, either intentionally or inadvertently.

A first rail 122 retains a column 124 of sanitary pads 126 includes a back wall 128 transversely attached sidewalls 130 and 132 which in turn are attached to respective vertically attached transversely extending front walls 134 and 136 to create a frame. At the lowermost end of the rail 122 is a dispenser 140 containing a shelf to prevent a sanitary pad from inadvertently falling out into the tray 54, unless specifically activated upon. At the top of the column 124 of a stack of the sanitary pads 126 is a weight 150 having a forward facing magnetic member 152.

A second rail 160 retains a column 162 of tampons 164 has a back wall 166 transversely attached sidewalls 168 and 170 which in turn are attached to respective vertically attached transversely extending front walls 172 and 174 to create a frame. At the lowermost end of the rail 160 is a dispenser 176 containing a shelf to prevent a tampon from inadvertently falling out into the tray 54, unless specifically activated upon. At the top of the column 162 of a stack of the sanitary pads 164 is a weight 180 having a forward facing magnetic member 182.

For each rail, there is a bottom shelf that prevents the stack from falling out without being pushed or activated and a weight on top of the stack which contains a forward extending magnet coming in contact with a transmission signal as will be discussed.

The first rail 122 is deeper than the second rail 160. The first rail retains the sanitary napkins, which are often located in a box. The second rail retains the tampons. For each rail, there is an aligned horizontal dispensing platform on which the lowest feminine hygiene product is retained with opposite blocking members which assist in dispensing the retained lowermost feminine hygiene product and assist in receiving the next lowermost feminine hygiene product on an oppositely disposed receiving platform. Each column further includes the top weight bearing platform thereon which forces the second lowermost feminine hygiene product onto the receiving platform after the lowermost feminine hygiene product has been dispensed into a receiving tray. For each column, the weight includes a magnet which comes in contact with an electronic signal to illuminate a light if a column of one of the sanitary hygiene products in out of product.

Each column/stack operates independent of the other. At the lowermost end of the first rail 122 is the dispensing member 140 to retain (and as will be described) the lowermost sanitary pad 126, which upon activation as will be described, will be pushed into the dispensing and receiving tray 54.

Spaced apart from first rail 122 retaining the column 124 of sanitary pads 126, there is the second rail 160 retaining the column/stack 162 of tampons 164. An interior wall 184 retains the power pack 88 and the motherboard 82.

FIG. 6 illustrates the condition when there are no more products contained in either rail. For instance, if the sanitary pad column 124 is completely out of sanitary pads 126, the first magnet 152 affixed to a first weight 150 engages a signal through a first reed switch 190 to cause the light 74 to shine on or through the front door 20 to show that the sanitary pad column 124 is out of sanitary pad stock. By way of example, the light 74 is red and is blinking. As can be seen in FIG. 6, the magnet 152 is in contact with the first reed switch 190.

In other embodiment, different types of sensors or sensor systems that determine a state of no more product being available are contemplated. For instance, a light detecting sensor, including a light source, such as a light emitting diode, and a photodiode, is contemplated. In other embodiment, a Hall-Effect sensor configured to determine a magnetic field is also contemplated.

If the tampon column 162 is completely out of tampons 164, the second magnet 182 affixed to a second weight 180 engages a signal through a reed switch 192 to cause the light 76 to shine on or through the front door 20 to show that the tampon column 162 is out of tampon stock. By way of example, the light 76 is red and is blinking. The second reed switch 192 is hardwired to the motherboard by a pair of wire leads from the second reed switch 192 to female connectors on the motherboard through a pair of hardwired leads. The first and second reed switches 190 and 192 provide a signal in the presence of a magnetic field to determine a location of the respective magnets.

Each of the weights 150 and 180 include dimensions such that the weight moves down the rail in which it is located with movement of the column of feminine hygiene products. In at least one embodiment, a bottom surface of the weight that engages the top feminine hygiene product in a column includes similar dimension of the product being contacted by the weight.

Figure 8:
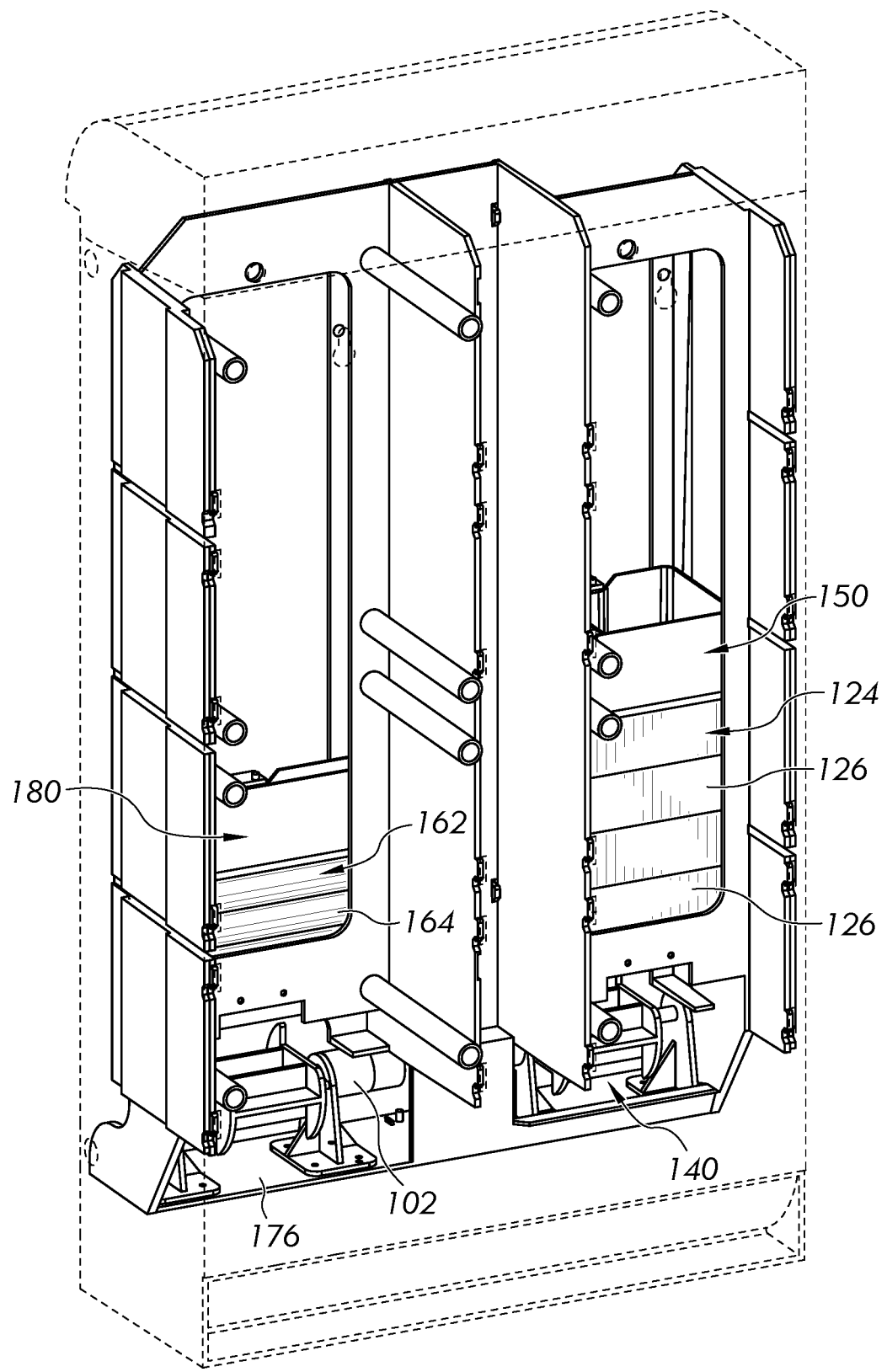
FIG. 8 is an internal rear elevational view illustrating several sanitary napkins in a rail with the lowermost sanitary napkin on a first dispenser and also illustrating several tampons in a rail with the lowermost tampon on a second dispenser.
Figure 9:
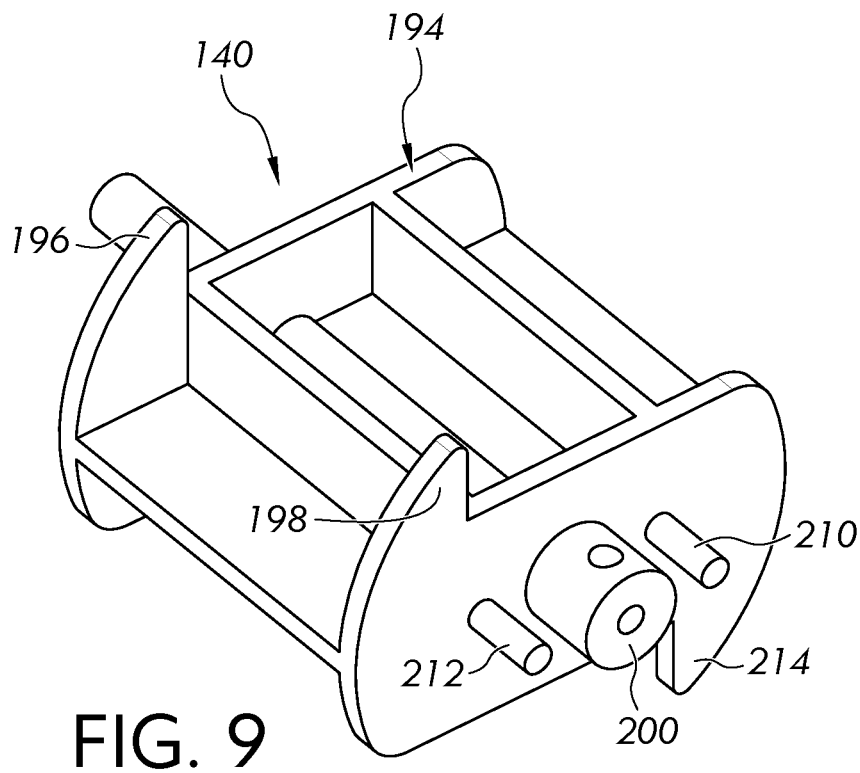
FIG. 9 is a perspective view of the product horizontal receiving member and dispensing member with an upper tray/platform and dispensing members.
Figure 10:
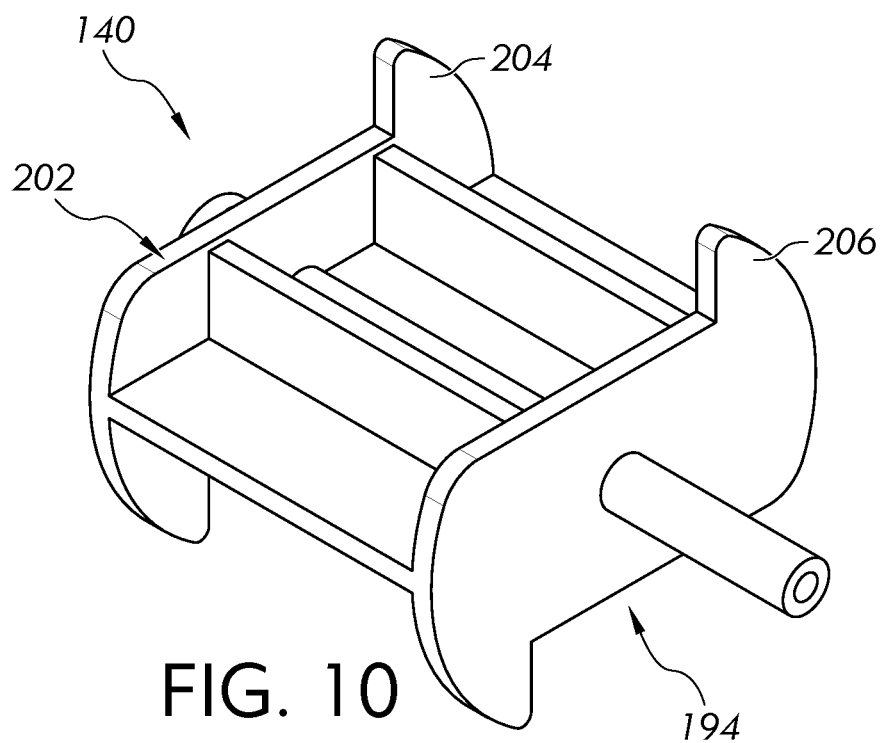
FIG. 10 is a perspective view of the product horizontal receiving member of FIG. 8 rotated one-hundred eighty degrees.

FIG. 8 illustrates an internal rear elevational view of several tampons 162 in the rail 160 with the lowermost sanitary napkin on the dispensing member 176.

With respect to the delivery of product to the tray 54, the dispensing member 140 has a first horizontal dispensing plate 194 (also called tray or platform) at the bottom of the column 124 of sanitary napkins 126. The dispensing apparatus 140 includes first and second blocking members 196 and 198 on which the lowermost sanitary napkin is retained with opposite blocking/dispensing members 196 and 198 respectively located at opposite ends of the first horizontal dispensing plate 194 which assist in dispensing the retained lowermost feminine napkin. The assembly includes a first shaft 200 affixed to a rotating portion of a first drive motor 92, the shaft 94. The shaft 200 has affixed at one location above the first rotating shaft 200, the above-described first horizontal plate 194 and its components. Affixed to an opposite side of and below the shaft 200 is a second horizontal dispensing plate 202 which is parallel to and aligned with first horizontal dispensing plate 194. The next sanitary napkin (once the one located on the plate 194 is dispense) is retained on horizontal dispensing plate 202 with opposite third and fourth blocking/dispensing members 204 and 206 respectively located at opposite ends of the second horizontal dispensing plate 202 which assist in dispensing the retained second lowermost sanitary napkin.

Figure 11:
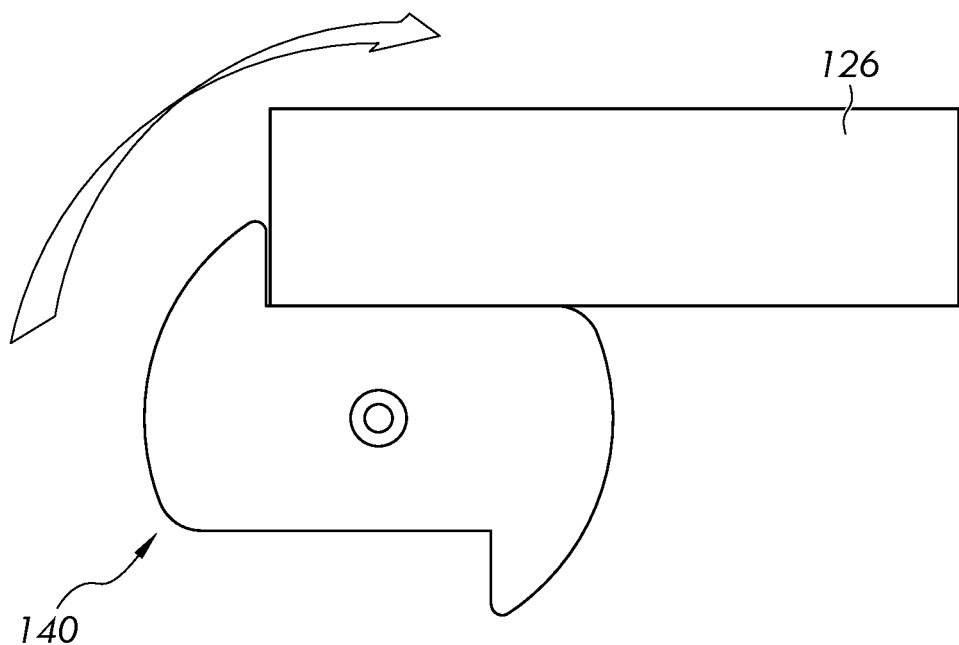
FIG. 11 is a side view of the product horizontal receiving member and dispensing member illustrated in FIG. 9 with a lowermost sanitary napkin on the first upper tray/platform.

In a starting position, the lowermost sanitary napkin rests on the first platform (also called plate) 194. A person waves a hand or makes a comparable motion in front of 50 on front surface of the door 20. The motion is received by the sanitary napkin motion sensor 96 in circuit board 84. An electrical signal is sent as previously described to the power pack 188 to be energized and to turn on motor 92 which causes the shaft 94 to rotate. The shaft 94 rotates in a clockwise direction by one-hundred eighty (180) degrees. See FIG. 11. The first horizontal platform 194 also rotates by one-hundred eighty (180) degrees so that the lowermost feminine napkin faces the bottom wall of the vending machine 10 and the opposite blocking/dispensing members 196 and 198 respectively push the lowermost feminine napkin onto a retrieving tray 54. The second horizontal plate 202 now faces the bottom of sanitary napkin column 124 and the second lowermost sanitary napkin is pushed by the weight 150 onto the second horizontal plate 202. Upon activation by a hand motion, the first drive motor 92 rotates shaft 94 by one-hundred eighty (180) degrees so that the second lowermost sanitary napkin is pushed onto the bottom wall and into the retrieving tray 54. The first micro-switch 90 (see FIG. 6) is contacted by either a first pin 210 or a second pin 212 which extends from a slide plate 214, or side wall) of the dispenser 140. Contact of one of the pins with the arm of the microswitch sends a signal to turn off the first motor 92 which in turn stops the rotation of first shaft 94 so that the dispenser is stationary. On the next action cycle when a person waves their hand in front of the sanitary napkin signal of the front cover 20, the cycle is repeated. The first motor 92 is caused to rotate by one-hundred eighty (180) degrees so that the first horizontal platform 194 faces the bottom the sanitary napkin column and is no longer in contract with the of the sanitary napkin products.

Either the sanitary napkin sensor circuit, circuit board 82, or controller 120 has a built in time delay to require a period of time, such as fifteen (15) seconds to one (1) minute between activation cycles. In one embodiment, the process is the same for the tampons 164 in the tampon column 162.

In a starting position, the lowermost tampon of the column 162 rests on a third platform (also called plate) 220 of dispenser 176. A person waves a hand or makes a comparable motion in front of symbol 52 on front surface of the front door 20. The motion is received by the tampon motion sensor 98 in tampon first circuit board 114. An electrical signal is sent to the power pack 88 to be energized to turn on second drive motor 102 which causes the shaft 104 to rotate. The shaft 104 is coupled to a shaft 222. The shaft 104 rotates in a clockwise direction by one-hundred eighty (180) degrees. The horizontal plate 220 also rotates by one-hundred eighty (180) degrees so that the lowermost tampon faces the receiving tray 54 of the vending machine 10 and opposite blocking/dispensing members 224 and 226 respectively push the lowermost tampon onto the retrieving tray 54. A fourth horizontal plate 228 now faces the bottom of tampon column and the second lowermost tampon is pushed by the weight 180 onto the fourth horizontal plate 228. Upon activation by a hand motion, the running motor 102 rotates shaft 104 by one-hundred eighty (180) degrees so that the second lowermost tampon is pushed onto the bottom wall and into the retrieving tray 54. The second micro-switch 100 sends a signal to turn off the second drive motor 102 which in turn stops the rotation of second shaft 104 so the apparatus is stationary. On the next action cycle when a person waves their hand in front of the symbol 52 of the front cover 20, the cycle is repeated.

Either the tampon sensor circuit board 96, circuit board 82, or control 120 has a built in time delay to require a period of time, such as fifteen (15) seconds to one (1) minute between activation cycles.

Figure 12:
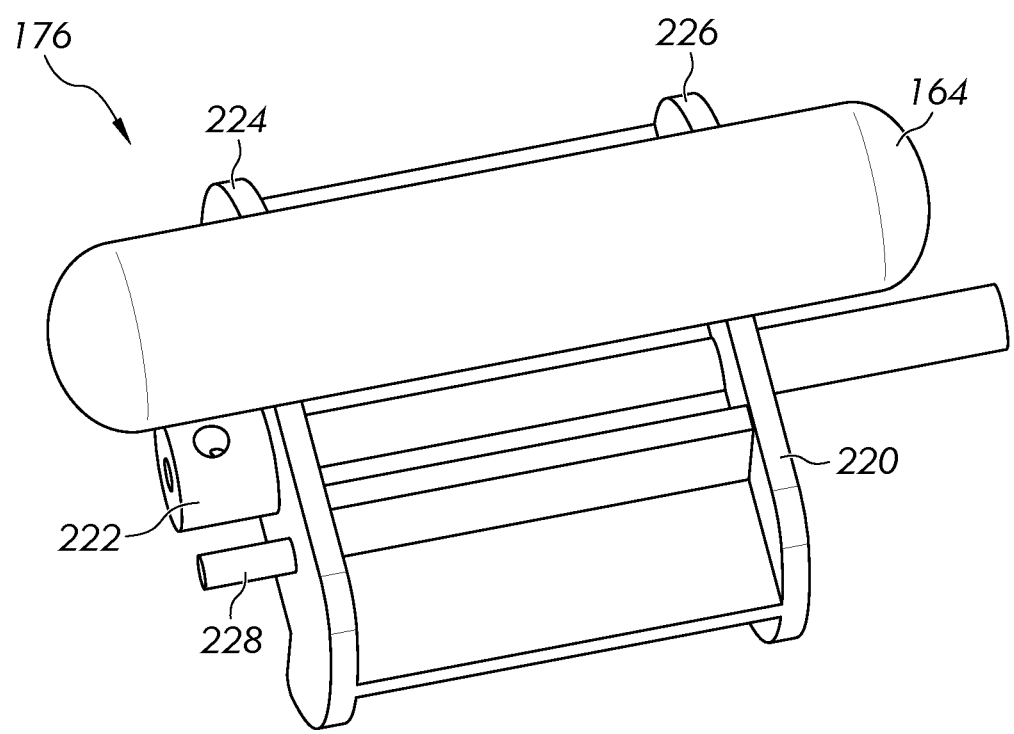
FIG. 12 is a perspective view of the product horizontal receiving member and dispensing member having a lowermost tampon on an upper tray/platform.

Similarly, for the column of tampons, the dispensing member 176 includes a pair of oppositely disposed teeth or pins 230 (one of which is shown in FIG. 12) which are affixed to the member 176. The one or pins 230 engages the microswitch 100, which cause the motor 102 to stop rotating.

If the tampon column 162 is completely out of tampons 164, the magnet 182 at the top of the sanitary pad column engages a signal in the circuit board 82 to cause a light 76 to shine on or through the front door 20 to indicate that the tampon supply is out of stock. By way of example, the light 76 is red and blinking.

If at least one battery dies or has a reduced power insufficient to power the dispenser 10, the power pack 88 is wired to a third light 232 through one of the circuit boards to a third light which remains on. Therefore, a person can see if the machine itself needs a replacement battery pack.

Through the present invention, an individual who is handicapped or has difficulty in even rotating a knob, or having to place coins in slots, can easily obtain the product by a simple motion of waving a hand in front of the sensor. The sensor can be set so that the person has to have the motion waved within 1 and ½ inch in front of the sensor so it will prevent someone simply walking by the machine to inadvertently dispense a feminine hygiene product. In addition, there will be built into a program in one of the circuit boards a timing sequence that after a product such as a feminine pad is dispensed, the next successive feminine pad cannot be dispensed for a period of such as 20 or 30 seconds. Similarly, a tampon is dispensed, the next successive tampon cannot be dispensed for a period of time such as 20 or 30 seconds. This will avoid someone from emptying the machine, either intentionally or inadvertently.

Insofar as the description above and the accompanying drawing disclose any additional subject matter that is not within the scope of the single claim below, the inventions are not dedicated to the public and the right to the one or more applications to claim such additional inventions is reserved.

Although a claim of different scope are presented herein, it should be recognized the scope of this invention is much broader than presented by the claims.

Of course the present invention is not intended to be restricted to any particular form or arrangement, or any specific embodiment, or any specific use, disclosed herein, since the same may be modified in various particulars or relations without departing from the spirit or scope of the claimed invention herein above shown and described of which the apparatus or method shown is intended only for illustration and disclosure of an operative embodiment and not to show all of the various forms or modifications in which this invention might be embodied or operated.

What is claimed is:

1. A method for dispensing sanitary hygiene products from a product dispenser, the method comprising:
    providing a first motion sensor for dispensing first sanitary hygiene products from a first row of first sanitary hygiene products with a first drive motor and a second motion sensor for dispensing second sanitary hygiene products from a second row of second sanitary hygiene products with a second drive motor, with each of the first motion sensor and the second motion sensor being configured to detect a motion provided by a moving object;
    providing an automatic time delay for the product dispenser;
    activating a first activation of a product dispensing with the first motion sensor to dispense one of the first sanitary hygiene products in response to only a first motion sensed by the first motion sensor;
    dispensing the one of the first sanitary hygiene products in response to the first motion sensed;
    activating a second activation of a product dispensing with the second motion senor to dispense one of the second sanitary hygiene products in response to only a second motion sensed by the second motion sensor;
    determining an activation time period between the activating the first activation and the activating the second activation;
    not dispensing the second sanitary hygiene product in response to the second motion if the automatic time delay has not elapsed when compared to the activation time period; and
    not dispensing another one of the first sanitary hygiene product in response to another motion sensed by the first motion sensor if the automatic time delay has not elapsed when compared to the activation time period.

2. The method of claim 1 further comprising dispensing the one of the second sanitary hygiene products in response to the second motion if the automatic time delay has elapsed when compared to the activation time period or dispensing the another one of the first sanitary hygiene product in response to an another motion sensed by the first motion sensor if the automatic time delay has elapsed when compared to the activation time period.

3. The method of claim 1 wherein the providing a first motion sensor and a second motion sensor includes wherein: i) the first motion sensor is configured to dispense the first product and not the second product in response to the first motion; and ii) the second motion sensor is configured to dispense the second product and not the first product in response to the second motion.

4. The method of claim 3 wherein the first sanitary hygiene products and the second sanitary hygiene products are different types of products, wherein the first motion sensor only activates the first activation of the first sanitary hygiene products, and the second motion sensor only activates the second activation of the second sanitary hygiene products.

5. The method of claim 3 wherein the first sanitary hygiene products and the second sanitary hygiene products are the same type of product.

6. The method of claim 3 further comprising dispensing the first sanitary hygiene product at a first aperture having a first product configuration and dispensing the second sanitary hygiene product at a second aperture having a second product configuration different than the first product configuration.

7. The method of claim 3 further comprising adjusting a first sensitivity of the first motion sensor and adjusting a second sensitivity of the second motion sensor such that the first motion does not affect the second motion sensor and the second motion does not affect the first motion sensor.

8. The method of claim 1 further comprising:
    identifying an opening time when a door of the sanitary hygiene product dispenser is moved to an open position; and
    not dispensing either the first product or the second product if the door is in the open position.

9. A method for dispensing sanitary hygiene products from a product dispenser, the method comprising:
    providing one or more motion sensors each being configured to detect a motion provided by a moving object;
    identifying a delay time;
    identifying a first time in response to a first motion sensed by one of the motion sensors;
    dispensing a first product in response to the first motion;
    identifying a second time in response to a second motion sensed by one of the motion sensors;
    determining an elapsed time between the first time and the second time;
    not dispensing a second product in response to the second motion if the elapsed time is less than the delay time;

identifying an opening time when a door of the product dispenser is moved to an open position; and not dispensing either the first product or the second product if the door is in the open position;

identifying a closing time when the door is moved to a close position;

identifying a third time in response to a third motion sensed by one of the motion sensors after the door is moved to the close position;

identifying an elapsed time between the closing time and the third motion time; and dispensing one of the first product or the second product if the elapsed time is greater than a delay time.

10. The method of claim 9 further comprising dispensing the second product in response to the second motion if the elapsed time is greater than the delay time.

11. The method of claim 10 wherein the providing one or more motion sensors includes providing: i) a first motion sensor configured to dispense the first product in response to the first motion; and ii) a second motion sensor configured to dispense the second product in response to the second motion.

12. The method of claim 11 wherein the first product and the second product are different types of products.

13. The method of claim 11 wherein the first product and the second product are the same type of product.

14. The method of claim 11 further comprising dispensing the first product at a first aperture having a first product configuration and dispensing the second product at a second aperture having a second product configuration different than the first product configuration.

15. The method of claim 11 further comprising adjusting a first sensitivity of the first motion sensor and adjusting a second sensitivity of the second motion sensor such that the first motion does not affect the second motion sensor and the second motion does not affect the first motion sensor.

16. A method for dispensing sanitary hygiene products from a sanitary hygiene product dispenser without requiring the insertion of any monetary compensation, the method comprising:

providing a machine having a cover, wherein the cover lacks a mechanism requiring the insertion of any monetary compensation to dispense sanitary hygiene products;

providing a first housing within the dispenser to accept a first row of sanitary hygiene products;

providing a second housing within the dispenser to accept a second row of sanitary hygiene products;

providing an automatic time delay for the sanitary hygiene product dispenser;

activating a first activation of a product dispensing with a first motion sensor to dispense one of the sanitary hygiene products only from the first row;

dispensing a first product in response to the first activation;

activating a second activation of a product dispensing with a second motion sensor to dispense one of the sanitary hygiene products only from the second row;

determining an activation time period between the activating the first activation and the activating the second activation; and not dispensing a second product in response to activating the second activation if the automatic time delay has not elapsed when compared to the activation time period, wherein the automatic time delay reduces the likelihood of or substantially prevents all of the sanitary hygiene products from being dispensed due to the automatic time delay.

17. The method of claim 16 further comprising dispensing the second product in response to the second activation once the automatic time delay has elapsed.

18. The method of claim 17 wherein the first product and the second product are different types of products, wherein the first activation activates dispensing of the first product, and the second activation activates dispensing of the second product.

19. The method of claim 17 wherein the first product and the second product are the same type of product.

* * * * *